United States Patent
Inoue

(10) Patent No.: US 12,226,200 B2
(45) Date of Patent: Feb. 18, 2025

(54) METHOD FOR DIAGNOSING GASTRO ESOPHAGEAL REFLUX DISEASE

(71) Applicants: OLYMPUS CORPORATION, Tokyo (JP); Haruhiro Inoue, Tokyo (JP)

(72) Inventor: Haruhiro Inoue, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 1276 days.

(21) Appl. No.: 16/426,713

(22) Filed: May 30, 2019

(65) Prior Publication Data

US 2020/0375485 A1 Dec. 3, 2020

(51) Int. Cl.
*A61B 5/03* (2006.01)
*A61B 1/015* (2006.01)
*A61B 1/273* (2006.01)

(52) U.S. Cl.
CPC .............. *A61B 5/037* (2013.01); *A61B 1/015* (2013.01); *A61B 1/2736* (2013.01)

(58) Field of Classification Search
CPC ..... A61B 5/037; A61B 5/4211; A61B 5/4842; A61B 5/4238; A61B 5/4233; A61B 1/015; A61B 1/2736; A61B 1/012; A61B 1/267; A61B 1/285; A61B 1/00006; A61B 1/0051; A61B 1/2733; A61B 10/04
See application file for complete search history.

(56) References Cited

U.S. PATENT DOCUMENTS

| | | | |
|---|---|---|---|
| 5,861,036 A | 1/1999 | Godin | |
| 5,907,093 A | 5/1999 | Lehmann | |
| 6,591,137 B1 | 7/2003 | Fischell et al. | |
| 6,663,639 B1 | 12/2003 | Laufer et al. | |
| 8,597,184 B2 | 12/2013 | Addington et al. | |
| 9,005,121 B2 | 4/2015 | Addington et al. | |
| 9,091,612 B2 | 7/2015 | Lehmann | |
| 9,226,878 B2 | 1/2016 | Elia et al. | |
| 9,295,395 B2 | 3/2016 | Elia et al. | |
| 2002/0062105 A1 | 5/2002 | Tanner et al. | |
| 2004/0138586 A1* | 7/2004 | Ganz | A61B 5/036 600/560 |

(Continued)

FOREIGN PATENT DOCUMENTS

| | | |
|---|---|---|
| JP | 10-507392 A | 7/1998 |
| JP | 2001-526916 A | 12/2001 |

(Continued)

OTHER PUBLICATIONS

Tu1170 Diagnostic Performance of an Endoscopic Pressure Integrated System (EPSIS): a Novel Diagnostic Tool for Gastroesophageal Reflux Disease—Gastrointestinal Endoscopy (giejournal.org) (Year: 2018).*

(Continued)

*Primary Examiner* — Aaron B Fairchild
*Assistant Examiner* — Megan Elizabeth Monahan
(74) *Attorney, Agent, or Firm* — Oliff PLC

(57) ABSTRACT

A method for diagnosing gastro esophageal reflux disease (GERD), comprising: introducing an endoscope into a stomach of a subject; measuring a pressure in the stomach while supplying gas into the stomach using the endoscope; and determining whether the subject has GERD or not based on a maximum value of the pressure and a wave pattern of a value of the pressure.

21 Claims, 3 Drawing Sheets

(56) References Cited

U.S. PATENT DOCUMENTS

| | | | |
|---|---|---|---|
| 2005/0096634 A1* | 5/2005 | Madsen | A61B 5/14539 604/118 |
| 2006/0259061 A1 | 11/2006 | Kick et al. | |
| 2006/0276812 A1 | 12/2006 | Hill et al. | |
| 2008/0208240 A1 | 8/2008 | Paz | |
| 2009/0316925 A1* | 12/2009 | Eisenfeld | H04R 1/46 381/67 |
| 2010/0249723 A1 | 9/2010 | Fangrow, Jr. | |
| 2012/0083650 A1 | 4/2012 | Raven | |
| 2013/0035740 A1* | 2/2013 | Sharma | A61N 1/36178 607/40 |
| 2013/0046150 A1 | 2/2013 | Devanaboyina | |
| 2018/0116912 A1 | 5/2018 | Zhang et al. | |

FOREIGN PATENT DOCUMENTS

| | | | |
|---|---|---|---|
| JP | 3248533 B2 | 1/2002 | |
| JP | 2003-530135 A | 10/2003 | |
| JP | 4082771 B2 | 4/2008 | |
| JP | 4498355 B2 | 7/2010 | |
| JP | 2010-537693 A | 12/2010 | |
| JP | 2011-510740 A | 4/2011 | |
| JP | 2012-505050 A | 3/2012 | |
| JP | 2013-517887 A | 5/2013 | |
| JP | 2015-109971 A | 6/2015 | |
| JP | 5798918 B2 | 10/2015 | |
| JP | 2017-509462 A | 4/2017 | |
| JP | 2017-522929 A | 8/2017 | |
| JP | 2018-515177 A | 6/2018 | |
| JP | 2018-164743 A | 10/2018 | |
| WO | 99/22783 A1 | 5/1999 | |
| WO | 00/59376 A1 | 10/2000 | |
| WO | 2009/027864 A1 | 3/2009 | |
| WO | 2009/096874 A1 | 8/2009 | |
| WO | WO-2010021690 A2 * | 2/2010 | A61B 5/11 |
| WO | 2010/042869 A1 | 4/2010 | |
| WO | 2011/092701 A1 | 8/2011 | |
| WO | 2015/037005 A1 | 3/2015 | |
| WO | 2015/143452 A1 | 9/2015 | |
| WO | 2015/188154 A1 | 12/2015 | |
| WO | 2016/127860 A1 | 8/2016 | |
| WO | 2016/164643 A1 | 10/2016 | |
| WO | 2017/184843 A1 | 10/2017 | |

OTHER PUBLICATIONS

Yield pressure_ a new concept in the evaluation of GERD_—Abstract—Europe PMC (Year: 1996).*

Gutschow et al., "Effect of aging on esophageal motility in patients with and without Gerd," GMS German Medical Science 2011, vol. 9 ISSN 1612-3174, hereinafter Gutschow. (Year: 2011).*

Gutschow et al., "Effect of aging on esophageal motility in patients with and without GERD," GMS German Medical Science 2001, vol. 9 ISSN 1612-3174, (Year: 2001).*

Tsubio et al., "Role of the lower esophageal sphincter on esophageal acid exposure—a review of over 2000 patients," Tropical Gastroenterology 2012 ;22(2):107-111, (Year: 2012).*

Ismail et al. "Endoscopic Appearance of the Gastroesophageal Valve and Competence of the Cardia." Diagnostic and Therapeutic Endoscopy, vol. 2, pp. 147-150, 1996.

Shimamura et al. "Diagnostic Performance of an Endoscopic Pressure Integrated System (EPSIS): A Novel Diagnostic Tool for Gastroesophageal Reflux Disease." Gastrointestinal Endoscopy, vol. 87, No. 6S, Tu1170, 2018.

Iwaya et al. J-CASE (Japan Consortium for Advanced Surgical Endoscopy), Nov. 3, 2018.

"The 96th Congress of Japan Gastroenterological Endoscopy Society." Digestive Endoscopy, vol. 30, pp. 817-830, Nov. 2018.

Inoue, Haruhiro. "Novel Tool of Endoscopic Diagnosis and Treatment for Esophagus." 98th Keio Medical Association General Meeting, Symposium, Nov. 10, 2018.

Ominami et al. "Present and Future of Endoscopic Observation." 104th Regular Meeting, Japanese Gastroenterological Endoscopy Society Kanto Branch, Jun. 10-11, 2017.

Inoue et al. "Novel Endoscopic Diagnosis (EPSIS) and Endoscopic Therapy (ARMS) for Refractory GERD." The 72nd Annual Meeting of the Japan Esophageal Society, Jun. 28-29, 2018.

Ominami et al. "Utility of Endoscopic Pressure Study Integrated System (EPSIS): Novel Functional Endoscopy for GERD Diagnosis." Digital Poster Session 69 (Japan Gastroenterological Endoscopy Society), JDDW2017, Oct. 14, 2017.

Vegesna et al. "Induced Opening of the Gastroesophageal Junction Occurs at a Lower Gastric Pressure in GERD Patients and in Hiatal Hernia Subjects than in Normal Control Subjects." Gastroenterology Research and Practice, pp. 1-6, 2010.

Benditt, Joshua O. "Esophageal and Gastric Pressure Measurements." Respiratory Care, vol. 50, No. 1, pp. 68-77, 2005.

Pandolfino et al. "Restoration of Normal Distensive Characteristics of the Esophagogastric Junction After Fundoplication." Annals of Surgery, vol. 242, No. 1, pp. 43-48, Jul. 2005.

Turnbull et al. "Intra-abdominal Pressure Measurement: Validation of Intragastric Pressure as a Measure of Intra-Abdominal Pressure." British Journal of Anaesthesia. vol. 98, pp. 628-634, 2007.

* cited by examiner

METHOD FOR DIAGNOSING GASTRO ESOPHAGEAL REFLUX DISEASE

BACKGROUND

This invention relates to a method for diagnosing gastro esophageal reflux disease (GERD).

GERD is a disease caused by a reflux of content of stomach including gastric acid into esophagus. Deterioration of cardia's function causes the reflux.

Twenty four-hour pH monitoring (24-hour pH monitoring) is a method for diagnosing GERD. In 24-hour pH monitoring, a patient has a tube inserted into his or her nose for 24 hours. This tube can often cause pain. Additionally, it takes a long time to diagnose GERD by using the 24-hour pH monitoring method.

SUMMARY

Exemplary embodiments relate to a method for diagnosing GERD. The method can include introducing an endoscope into a stomach of a subject, measuring a pressure in the stomach while supplying gas into the stomach using the endoscope, and determining whether the subject has GERD or not based on a maximum value of the pressure in the stomach and a wave pattern of a value of the pressure in the stomach.

DETAILED DESCRIPTION

An embodiment of the present invention shall be described with reference to FIGS. 1 to 5.

Figure 1:
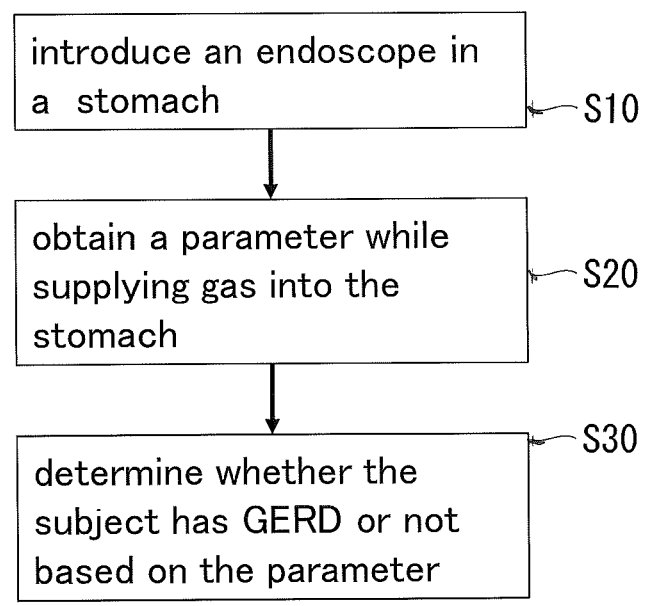
FIG. 1 is a flowchart showing a flow of the method for diagnosing GERD according to one aspect of the present invention.

FIG. 1 is a flowchart showing a flow of the method for diagnosing GERD (hereinafter, simply referred as "diagnosing method") according to the embodiment of the present invention. First, in step S10, an operator inserts an endoscope into a subject from a natural orifice such as mouth and nose, and introduces a distal portion of the endoscope in a stomach. A known flexible endoscope can be used in this procedure.

Next, in step S20, the operator obtains a parameter of the subject while increasing pressure in the stomach by supplying gas into the stomach. Gas-supplying function of the endoscope can be used in this procedure.

Cardia starts to close when the pressure in the stomach increases. Since a healthy cardia is able to keep its closing state against a high pressure, the pressure in the stomach increases as gas is supplied into the stomach. However, in GERD patients, the pressure in the stomach does not increase more than a certain value because their malfunction of the lower esophagus sphincter (LES). The volume of the gas supplied into the stomach is set to an extent in that a body reflex of closing cardia occurs in a healthy person, which is greater than a volume supplied into a stomach in an ordinary endoscopic observation. A paper "Endoscopic appearance of the Gastroesophageal valve and competence of the cardia", Diagnostic and Therapeutic Endoscopy, 1996, Vol. 2, pp. 147-150, reports that pressure value of a stomach when cardia opens during gas-supply is deteriorated in GERD patients.

The method focuses on this phenomenon and obtains parameters while supplying gas into a stomach. GERD can be diagnosed based on the obtained parameters.

Figure 2:
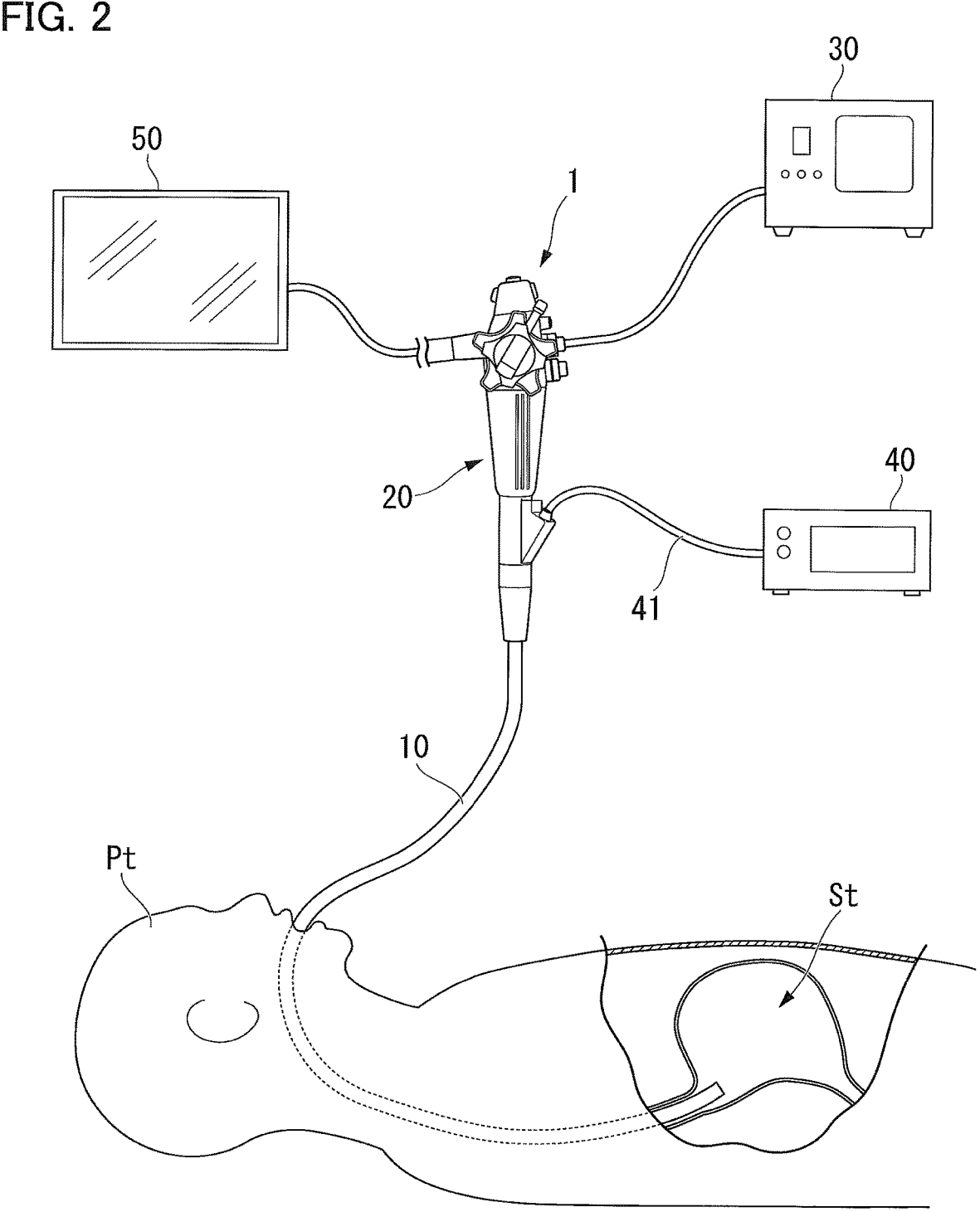
FIG. 2 is a schematic diagram showing a state in which an endoscope is introduced into a stomach.

An example of the step S10 is schematically shown in FIG. 2. An endoscope 1 inserted into the subject Pt comprises an elongated insertion portion 10, a manipulation portion 20 connected to the insertion portion, and a display portion 50 connected to the manipulation portion 20. A gas-supply mechanism 30 and a pressure measuring mechanism 40 are attached to the endoscope 1. The gas-supply mechanism 30 is connected to a first channel of the endoscope 1. A tube 41 is connected to the pressure measuring mechanism 40 and inserted into a second channel of the endoscope 1. A distal end of the tube 41 (not shown) locates in the second channel.

The aforementioned configuration makes it possible to supply gas from the endoscope 1 into the stomach St of the subject Pt and measuring pressure in the stomach St by the pressure measuring mechanism 40 using the tube 41.

The tube 41 may be protruded outside the endoscope 1 from the second channel. The tube 41 may be omitted by directly connecting the pressure measuring mechanism 40 to the second channel of the endoscope 1. Since the stomach St and the second channel communicate in this diagnosing method, a pressure value in the second channel can be used as an alternative index of the pressure in the stomach St.

The operator stops the gas supply into the stomach St when a predetermined conditions are fulfilled. If necessary, the operator aspires gas and decrease the pressure in the stomach St. Examples of the predetermined conditions can be shown as follows:

The pressure value in the stomach reaches a predetermined value.

A predetermined period of time elapses while the pressure value does not reach the predetermined value.

From a viewpoint in avoiding an excess stress to a stomach and a cardia, it is preferable that the predetermined value is set equal to or less than 20 mm mercury (mmHg). The predetermined period of time may be set to 10 to 600 seconds.

After that, the operator removes the endoscope 1 from the subject Pt.

The operator obtains a maximum pressure value in the stomach in step S20. If the gas supply is stopped because the pressure value reaches the predetermined value, the maximum value becomes the predetermined value.

In step S30, the operator or another diagnose determines whether the subject Pt has GERD or not using the parameters obtained in the step S20. The step S30 may be carried out after removing the endoscope 1.

When the pressure in the stomach is used in the diagnosing method, the obtained maximum value is compared with a threshold value for example. In this case, the subject is classed as "healthy" when the maximum value is equal to or greater than the threshold value, and is classed as "suspect of GERD" when the maximum value is less than the threshold value. The threshold value can be set concerning sex, age, and body size of the subject, for example 15 mmHg to 20 mmHg.

The threshold value may be lower than the predetermined value. The threshold value may be equal to the predetermined value. The gas supply and diagnosis become easy when the predetermined value is greater than the threshold value by 1 to 5 mmHg.

The operator finally determined which of "suspect of GERD" and "healthy" the subject is classed as, by combining the aforementioned classification and more than one sub finding. The sub findings in the present embodiment are shown as follows.

a. A Waveform of the Pressure in the Stomach in Step S20

The operator obtains a change over time in the pressure in the stomach during the step S20 by the pressure measuring mechanism 40 or the like.

Figure 3:
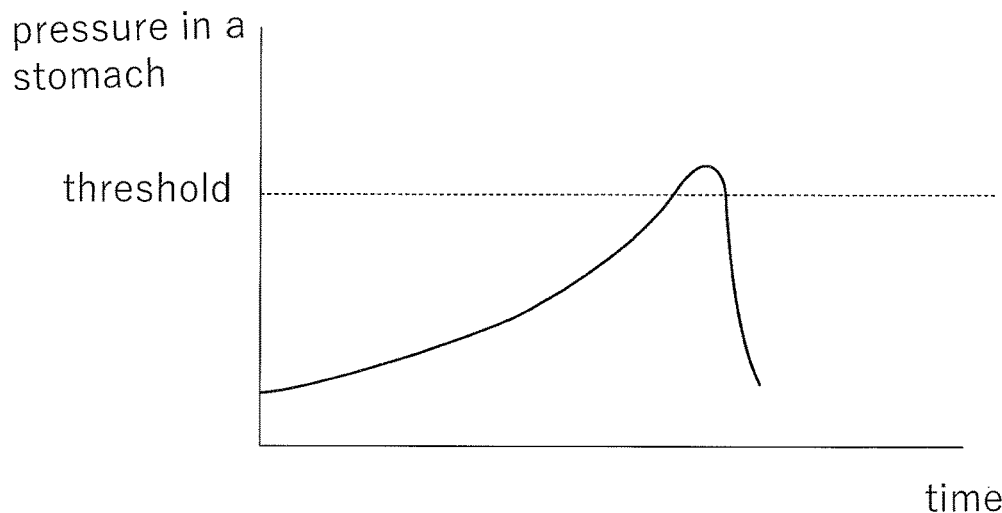
FIG. 3 shows an example of a waveform of a pressure in a healthy person's stomach.

An example of the waveform of the pressure in a stomach in a healthy person is shown in FIG. 3. In a healthy person of normal LES function, the waveform shows a tendency of increasing to the predetermined value without decreasing after the step S20 starts.

Figure 4:
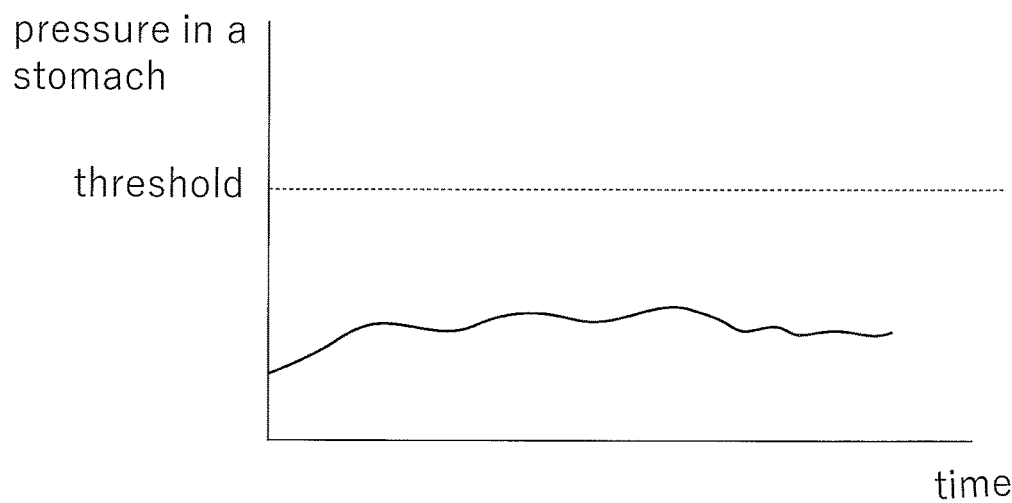
FIG. 4 shows an example of a waveform of a pressure in a GERD patient's stomach.

An example of the waveform of the pressure in a stomach in a GERD patient is shown in FIG. 4. In a GERD patient of deteriorated LES function, the waveform repeats increase and decrease in a certain pressure range because cardia opens before the pressure value reaches the predetermined value. As a result, the waveform becomes flat compared to that of a healthy person.

Accordingly, the waveform of the pressure in the stomach can be used as a sub finding. Several parameters in the change over time of the pressure in a stomach can be utilized as sub findings, alternative to the waveform or combined with the waveform. Examples of the parameters can be shown as follows.

Time elapsed that the pressure in the stomach reaches the predetermined value

A proportion of flat wave during the step S20

An average pressure value in the flat wave

A difference of the maximum value and the minimum value of the pressure in the stomach (a maximum amplitude)

A maximum amplitude in a healthy person is likely to be more than twice of that in a GERD patient.

b. An Endoscopic View of Cardia in the Step S20

In the step S20, the operator orientates the distal end of the endoscope 1 to the cardiac portion and observes the cardia by the endoscope 1.

In a healthy person, the operator is able to observe that the cardia surrounding the insertion portion is firmly closed in the step S20. When the predetermined value is set as a high value, the cardia may temporally open. Even in that case, the operator is able to observe that esophagus flutters and closes from its mouth-side.

In a GERD patient, loosening and partial opening of the cardia are observed in the step S20. When the esophagus is seen through the opening, the esophagus may not flutter or may show a weak fluttering.

Accordingly, the endoscopic view of cardia during pressurizing inside the stomach can be used as a sub finding.

c. A Burp Sound in the Step S20

During the step S20, when air in the stomach leaks from the cardia, a burp sound is heard. This burp sound is generated by vibration of cardia, esophagus, pharynx, or larynx. The generated burp sound can be continuously obtained by a sensor attached to the subject Pt, such as on its neck.

Following parameters about the burp sound can be a sub findings.

Length of the burp sound: Length of the burp sound is likely to be short in healthy person, while it is likely to be long in a GERD patient. An elapsed time of the longest burp sound and a ratio of a period in which the burp sound is heard in the step S20 can be shown as an example of the parameter.

Volume of the burp sound: Volume of the burp sound is likely to be high in healthy person, because a large amount of air leaks at one time. Volume of the burp sound is likely to be low in a GERD patient because of continuous leaking of air. A value of a maximal volume of the burp sound or an average volume of the burp sound can be shown as an example of the parameter. Volume evaluation such as whether the maximal volume of the burp sound or the average volume of the burp sound is equal to or greater than a predetermined threshold value or not also can be shown as an example of the parameter.

The aforementioned sub findings can be obtained during the step S20 in parallel. All the sub findings may be obtained in the step S20 and some of the sub findings may be selected for combining with the classification. The sub findings may be obtained by another gas supply which is distinct from the step S20.

An order in priority may be set to a plurality of the sub findings. The sub findings combined with the classification may be increased along the order in priority when the operator finds difficulty in the determination.

As described, the diagnosing method according to the present embodiment can be carried out by introducing an endoscope in stomach and supplying gas into the stomach by a volume greater than a volume in an ordinary endoscopic procedure. Therefore, burden and pain of a subject is extremely lower than that in the 24-hour pH monitoring.

All the information used in the diagnosis can be obtained within about ten minutes, including sub findings in the present diagnosing method. The operator is able to diagnose within an hour and it is not difficult. The present diagnosing method is far better than the 24-hour pH monitoring in this aspect.

Since the present diagnosing method is carried out using an endoscope, it can be carried out with an endoscopic observation of the mucosa of esophagus-stomach junction, continuously or in parallel. As a result, the present diagnosing method is able to diagnose not only GERD in which an inflammatory finding is seen, but also a broader gastro esophageal reflux disease including non-erosive esophageal reflux disease (NERD) in which an inflammatory finding is not seen.

The present invention is not limited to what is described. Additions, omissions, substitutions, and other modifications can be made without departing from the spirit or scope of the present invention. Accordingly, the present invention is only limited by the scope of the appended claims.

For example, gas in the stomach may be removed partially or entirely before the step S20, in order to decrease noise in measuring pressure in the stomach or the like.

In the diagnosing method according to the present invention, whether the subject has GERD or not may be diagnosed using one or more sub findings without using the maximum pressure value in the stomach.

Figure 5:
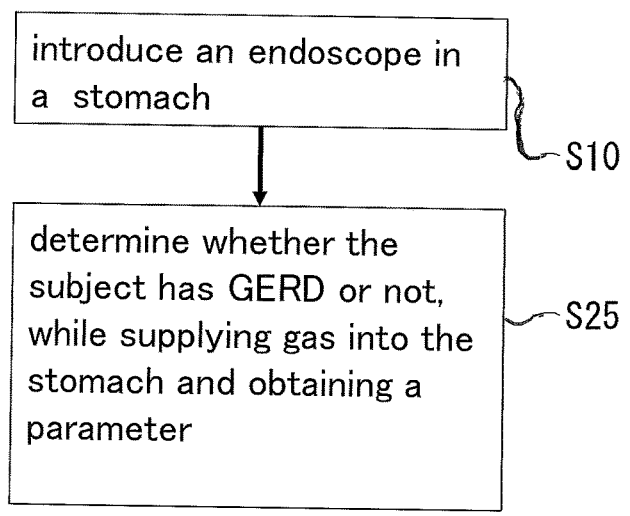
FIG. 5 is a flowchart showing a flow of the method for diagnosing GERD according to an exemplary embodiment.

The step S20 and the step S30 may be carried out simultaneously or in parallel after the step S10, shown as a step S25 in FIG. 5.

What is claimed is:

1. A method for diagnosing gastro esophageal reflux disease (GERD), comprising:

identifying a threshold value of an internal pressure within a stomach of a person without GERD;

obtaining a first waveform of time-series change of the internal pressure within the stomach of the person without GERD, wherein the first waveform of time-series change increases to the threshold value when gas is supplied into the stomach;

obtaining a second waveform of time-series change of an internal pressure within a stomach of a person with GERD, wherein the second waveform of time-series change repeatedly increases and decreases within a pressure range when gas is supplied into the stomach and the second waveform of time-series change is flatter than the first waveform of time-series change;

inserting an endoscope into a stomach of a subject;

supplying a volume of gas substantially identical to a volume of gas which causes a person without GERD to have a body reflex of a closing cardia;

measuring an internal pressure only within the stomach of the subject while supplying gas into the stomach of the subject using the endoscope to obtain a waveform of time-series change of the internal pressure value of the subject, the internal pressure including a maximum value of the internal pressure in the stomach of the subject;

obtaining a third waveform of time-series change of the internal pressure value in the stomach of the subject;

comparing the maximum value of the subject to the threshold value of the person without GERD;

comparing the third waveform of time-series change to the first waveform of time-series change;

comparing the third waveform of time-series change to the second waveform of time-series change;

determining whether the subject has GERD based on the comparison of the maximum value of the subject to the threshold value of the person without GERD, the comparison of the third waveform of time-series change to the first waveform time-series change, and the comparison of the third waveform of time-series change to the second waveform of the time-series change.

2. The method for diagnosing GERD according to claim 1, further comprising:
observing a cardia of the subject by the endoscope while supplying gas into the stomach using the endoscope; and
determining whether the subject has GERD based on the maximum value of the internal pressure, the waveform of time-series change of the internal pressure value, and a result of a cardia observation.

3. The method for diagnosing GERD according to claim 1, further comprising:
obtaining a burp sound of the subject while supplying gas into the stomach using the endoscope; and
determining whether the subject has GERD based on the maximum value of the internal pressure, the waveform of the internal pressure value, and the burp sound.

4. The method for diagnosing GERD according to claim 1, wherein the measuring an internal pressure in the stomach includes measuring a pressure in a channel of the endoscope.

5. The method for diagnosing GERD according to claim 1, further comprising:
comparing the maximum value of the internal pressure with the threshold value; and
determining that the subject has GERD when the maximum value of the internal pressure is below the threshold value.

6. The method for diagnosing GERD according to claim 1, wherein determining whether the subject has GERD is based on a volume or length of a burp sound.

7. A method for diagnosing gastro esophageal reflux disease (GERD), comprising:
identifying a threshold value of an internal pressure within a stomach of a person without GERD,
obtaining a first waveform of time-series change of the internal pressure within the stomach of the person without GERD, wherein the first waveform of time-series change increases to the threshold value when gas is supplied into the stomach
obtaining a second waveform of time-series change of an internal pressure within a stomach of a person with GERD, wherein the second wave form of time-series change repeatedly increases and decreases within a pressure range when gas is supplied into the stomach and the second waveform of time-series change is flatter than the first waveform of time-series change;
inserting an endoscope into a stomach of a subject;
supplying a volume of gas into the stomach using the endoscope;
measuring an internal pressure only within the stomach of the subject while supplying gas into the stomach using the endoscope to obtain a waveform of time-series change of the internal pressure value of the subject, the internal pressure including
a maximum value of the internal pressure in the stomach of the subject;
obtaining a third waveform of time-series change of the internal pressure value in the stomach of the subject;
comparing the maximum value of the subject to the threshold value of the person without GERD;
comparing the third waveform of time-series change to the first waveform of time-series change;
comparing the third waveform of time-series change to the second waveform of time-series change;
determining whether the subject has GERD based on the comparison of the maximum value of the subject to the threshold value of the person without GERD, the comparison of the third waveform of time-series change to the first waveform time-series change, and the comparison of the third waveform of time-series change to the second waveform of the time-series change.

8. The method for diagnosing GERD according to claim 7, further comprising:
observing a cardia of the subject by the endoscope while supplying gas into the stomach using the endoscope; and
determining whether the subject has GERD based on the maximum value of the internal pressure, the waveform of time-series change of the internal pressure value, and a result of a cardia observation.

9. The method for diagnosing GERD according to claim 7, further comprising:
obtaining a burp sound of the subject while supplying gas into the stomach using the endoscope; and
determining whether the subject has GERD based on the maximum value of the internal pressure, the waveform of time-series change of the internal pressure value, and the burp sound.

10. The method for diagnosing GERD according to claim 7, wherein the measuring an internal pressure in the stomach includes measuring a pressure in a channel of the endoscope.

11. The method for diagnosing GERD according to claim 7, further comprising:

comparing the maximum value of the internal pressure with the threshold value; and determining that the subject has GERD when the maximum value of the internal pressure is below the threshold value.

12. The method for diagnosing GERD according to claim 7, wherein determining whether the subject has GERD is based on a volume or length of a burp sound.

13. The method for diagnosing GERD according to claim 6, wherein a length of the burp sound of the subject with GERD is longer than a length of the burp sound of the person without GERD.

14. The method for diagnosing GERD according to claim 12, wherein a length of the burp sound of the subject with GERD is longer than a length of the burp sound of the person without GERD.

15. A method for diagnosing gastro esophageal reflux disease (GERD), comprising:
  identifying a threshold value of an internal pressure within a stomach of a person without GERD,
  obtaining a first waveform of time-series change of the internal pressure within the stomach of the person without GERD, wherein the first waveform of time-series change increases to the threshold value when gas is supplied into the stomach
  obtaining a second waveform of time-series change of an internal pressure within a stomach of a person with GERD, wherein the second waveform of time-series change repeatedly increases and decreases within a pressure range when gas is supplied into the stomach and the second waveform of time-series change is flatter than the first waveform of time-series change;
  inserting an endoscope into a stomach of a subject;
  supplying a volume of gas substantially identical to a volume of gas which causes a person without GERD to have a body reflex of a closing cardia;
  measuring an internal pressure only within the stomach of the subject while supplying gas into the stomach of the subject using the endoscope to obtain a waveform of time-series change of the internal pressure value of the subject, the internal pressure including a maximum value of the internal pressure in the stomach of the subject;
  obtaining a third waveform of time-series change of the internal pressure value in the stomach of the subject;
  comparing the maximum value of the subject to the threshold value of the person without GERD;
  comparing the third waveform of time-series change to the first waveform of time-series change; and
  determining whether the subject has GERD based on the comparison of the maximum value of the subject to the threshold value of the person without GERD, the comparison of the third waveform of time-series change to the first waveform time-series change, and the comparison of the third waveform of time-series change to the second waveform of the time-series change.

16. The method for diagnosing GERD according to claim 1, further comprising:
  determining that the subject has GERD while supplying gas into the stomach.

17. The method for diagnosing GERD according to claim 1, further comprising:
  measuring an internal pressure value in the stomach including a maximum value of the internal pressure in the stomach and obtaining a waveform of time-series change of the internal pressure value while supplying gas into the stomach.

18. The method for diagnosing GERD according to claim 1, further comprising:
  supplying gas into the stomach to measure the internal pressure value in the stomach including the maximum value of the internal pressure in the stomach and obtain the waveform of time-series change of the internal pressure value.

19. The method for diagnosing GERD according to claim 7, further comprising:
  determining that the subject has GERD while supplying gas into the stomach.

20. The method for diagnosing GERD according to claim 7, further comprising:
  measuring an internal pressure value in the stomach including a maximum value of the internal pressure in the stomach and obtaining a waveform of the internal pressure value while supplying gas into the stomach.

21. The method for diagnosing GERD according to claim 1, further comprising diagnosing GERD within a time period that is less than one hour.

* * * * *

UNITED STATES PATENT AND TRADEMARK OFFICE
CERTIFICATE OF CORRECTION

PATENT NO. : 12,226,200 B2
APPLICATION NO. : 16/426713
DATED : February 18, 2025
INVENTOR(S) : Haruhiro Inoue Page 1 of 1

It is certified that error appears in the above-identified patent and that said Letters Patent is hereby corrected as shown below:

On the Title Page

Item (73) change:
"(73) Assignee: OLYMPUS CORPORATION, Tokyo (JP)"
To:
-- (73) Assignee: OLYMPUS CORPORATION, Tokyo (JP)
          Haruhiro Inoue, Tokyo (JP) --

Signed and Sealed this
Twenty-ninth Day of July, 2025

Coke Morgan Stewart
*Acting Director of the United States Patent and Trademark Office*